(12) United States Patent
Zeikus et al.

(10) Patent No.: US 7,713,730 B2
(45) Date of Patent: May 11, 2010

(54) PNEUMATIC BIOREACTOR

(75) Inventors: J. Gregory Zeikus, Okemos, MI (US);
Kyungnam Kim, KyunKi-Do (KR);
Thomas A. Post, Pittsford, NY (US);
Keith E. Johnson, North Canton, OH (US)

(73) Assignee: PBS Biotech, Inc., Camarillo, CA (US)

( * ) Notice: Subject to any disclaimer, the term of this patent is extended or adjusted under 35 U.S.C. 154(b) by 326 days.

(21) Appl. No.: 11/739,659

(22) Filed: Apr. 24, 2007

(65) Prior Publication Data

US 2008/0268530 A1 Oct. 30, 2008

(51) Int. Cl.
*C12M 1/06* (2006.01)

(52) U.S. Cl. ............... 435/289.1; 366/102; 366/169.1; 366/175.1; 435/296.1

(58) Field of Classification Search ............... 366/102, 366/169.1, 175.1; 435/289.1
See application file for complete search history.

(56) References Cited

U.S. PATENT DOCUMENTS

| | | | |
|---|---|---|---|
| 29,149 | A | 7/1860 | Durham |
| 211,143 | A | 1/1879 | Fogarty |
| 257,505 | A | 5/1882 | McMillan et al. |
| 271,040 | A | 1/1883 | Cook |
| 272,656 | A | 2/1883 | Cook |
| 384,568 | A * | 6/1888 | Evans ............... 366/171.1 |
| 650,063 | A | 5/1900 | Kersten |
| 3,498,762 | A | 3/1970 | Van der Schee et al. |
| 3,715,885 | A | 2/1973 | Schur |
| 3,722,185 | A | 3/1973 | Miczek |

(Continued)

FOREIGN PATENT DOCUMENTS

EP 0617120 A2 9/1994

(Continued)

OTHER PUBLICATIONS

Singapore (Australian) Cover Sheet, Search Report, Written Opinion, and Citation Annexes for corresponding Singapore Patent Application No. SG 200802702-1, 7 pages (mailed Apr. 28, 2009).

(Continued)

*Primary Examiner*—William H Beisner
*Assistant Examiner*—Michael Hobbs
(74) *Attorney, Agent, or Firm*—Rothwell, Figg, Ernst & Manbeck, PC

(57) ABSTRACT

A pneumatic bioreactor having a containment vessel which includes a semi-cylindrical concavity defined by the vessel bottom. A mixing apparatus includes a rotational mixer rotatably mounted within the containment vessel about a horizontal axis. The rotational mixer has buoyancy-driven mixing cavities which are fed by a gas supply beneath the rotational mixer. The mixing apparatus extends into the semi-cylindrical concavity to substantially fill that concavity. The rotational mixer is divided into two wheels with outer paddles extending axially outwardly and inner paddles extending axially inwardly on either side of each wheel. Blades between the outer and inner paddles form impellers in the wheels to induce axial flow through the wheels in opposite directions. Stationary baffles fixed relative to the containment vessel are inclined toward the rotational mixer in the direction of rotation. The containment vessel may be of film and supported by a structural housing also having a semi-cylindrical concavity defined by the housing bottom.

4 Claims, 4 Drawing Sheets

U.S. PATENT DOCUMENTS

| | | | |
|---|---|---|---|
| 3,786,781 A | 1/1974 | Poulsen | |
| 3,788,616 A | 1/1974 | Clough, Jr. | |
| 3,886,074 A | 5/1975 | Prosser | |
| 3,911,064 A | 10/1975 | McWhirter et al. | |
| 3,930,816 A | 1/1976 | Miczek | |
| 3,990,870 A | 11/1976 | Miczek | |
| 4,053,141 A | 10/1977 | Gussefeld | |
| 4,054,031 A | 10/1977 | Johnson | |
| 4,095,426 A | 6/1978 | Rhodes | |
| 4,101,384 A | 7/1978 | Faust et al. | |
| 4,160,736 A | 7/1979 | Prosser | |
| 4,170,114 A | 10/1979 | Pruett | |
| 4,196,590 A | 4/1980 | Fries | |
| 4,203,961 A | 5/1980 | Cowley | |
| 4,223,094 A | 9/1980 | Vaseen | |
| 4,245,473 A | 1/1981 | Sandoval | |
| 4,246,753 A | 1/1981 | Redmond | |
| 4,266,402 A | 5/1981 | Pruett | |
| 4,268,385 A | 5/1981 | Yoshikawa | |
| 4,284,503 A | 8/1981 | Stahler | |
| 4,326,132 A | 4/1982 | Bokel | |
| 4,363,212 A | 12/1982 | Everett | |
| 4,416,546 A | 11/1983 | Parkins | |
| 4,540,491 A | 9/1985 | Zimmer | |
| 4,595,296 A | 6/1986 | Parks | |
| 4,655,603 A | 4/1987 | Palm | |
| 4,668,387 A | 5/1987 | Davie et al. | |
| 4,779,990 A | 10/1988 | Hjort et al. | |
| 4,919,849 A | 4/1990 | Litz et al. | |
| 4,944,596 A | 7/1990 | DeChristopher | |
| 4,956,082 A * | 9/1990 | Choi | 210/150 |
| 5,075,234 A | 12/1991 | Tunac | |
| 5,081,035 A | 1/1992 | Halberstadt et al. | |
| 5,156,778 A | 10/1992 | Small | |
| 5,198,156 A | 3/1993 | Middleton et al. | |
| 5,326,459 A * | 7/1994 | Hlavach et al. | 210/150 |
| 5,570,517 A | 11/1996 | Luker | |
| 5,605,400 A | 2/1997 | Kojima | |
| 5,632,962 A | 5/1997 | Baker et al. | |
| 5,755,961 A | 5/1998 | Limcaco | |
| 5,755,976 A | 5/1998 | Kortmann | |
| 5,756,012 A | 5/1998 | McGlashan et al. | |
| 5,791,780 A | 8/1998 | Bakker | |
| 5,939,313 A | 8/1999 | Cheng | |
| 6,036,355 A | 3/2000 | Yant et al. | |
| 6,036,357 A | 3/2000 | Van Drie | |
| 6,135,629 A | 10/2000 | Dohmann | |
| 6,140,615 A | 10/2000 | Matsumoto | |
| 6,195,991 B1 | 3/2001 | DeShon | |
| 6,237,898 B1 | 5/2001 | Lafont | |
| 6,305,165 B1 | 10/2001 | Mizuki, Sr. | |
| 6,361,202 B1 | 3/2002 | Lee et al. | |
| 6,392,072 B1 | 5/2002 | Henriksen | |
| 6,406,624 B1 | 6/2002 | DeVos | |
| 6,439,756 B1 | 8/2002 | Forschner et al. | |
| 6,447,243 B1 | 9/2002 | Kittle | |
| 6,599,426 B2 | 7/2003 | Drie | |
| 6,673,532 B2 | 1/2004 | Rao | |
| 6,926,437 B2 | 8/2005 | Drie | |
| 7,083,324 B2 | 8/2006 | Van Drie | |
| 7,083,720 B2 | 8/2006 | Miller | |
| 7,201,884 B2 | 4/2007 | Cohen | |
| 2002/0110915 A1 | 8/2002 | Shaaltiel | |
| 2003/0161216 A1 | 8/2003 | Gigas et al. | |
| 2005/0158851 A1 | 7/2005 | Furey | |
| 2005/0201202 A1 | 9/2005 | Drie | |
| 2005/0258083 A1 | 11/2005 | Miller | |
| 2005/0272146 A1 | 12/2005 | Hodge et al. | |
| 2008/0261299 A1* | 10/2008 | Zeikus et al. | 435/289.1 |

FOREIGN PATENT DOCUMENTS

| | | |
|---|---|---|
| EP | 1120460 A1 | 8/2001 |
| JP | 60-164476 | 8/1985 |
| WO | WO 2007111677 A2 | 10/2007 |

OTHER PUBLICATIONS

International Search Report, and Written Opinion for PCT Patent Application No. PCT/US2008/005010, 15 pages (mailed May 15, 2009).

* cited by examiner

PNEUMATIC BIOREACTOR

BACKGROUND OF THE INVENTION

The field of the present invention is bioreactors with mixing.

Efforts of biopharmaceutical companies to discover new biological drugs have increased exponentially duwheel the past decade. Most biological drugs are produced by cell culture or microbial fermentation processes which require sterile bioreactors and an aseptic culture environment. However, shortages of global biomanufactuwheel capacity are anticipated in the foreseeable future. An increasing number of biological drug candidates are in development. Stwheelent testing, validation, and thorough documentation of process for each drug candidate are required by FDA to ensure consistency of the drug quality used for clinical trials to the market. Further, production needs will increase as such new drugs are introduced to the market. Bioreactors have also been used for cultivation of microbial organisms for production of various biological or chemical products in the beverage and biotechnology industries as well as for pharmaceuticals.

Stainless steel stir tanks have been the only option for large scale production of biological products in suspension culture. Manufactuwheel facilities with conventional stainless bioreactors, however, require large capital investments for construction, high maintenance costs, long lead times, and inflexibilities for changes in manufactuwheel schedules and production capacities.

A production bioreactor contains culture medium in a sterile environment that provides various nutrients required to support growth of the biological agents of interest. Conventional bioreactors use mechanically driven impellers to mix the liquid medium duwheel cultivation. The bioreactors can he reused for the next batch of biological agents after cleaning and sterilization of the vessel. The procedure of cleaning and sterilization requires a significant amount of time and resources. The problems with sterilization are compounded by the need to monitor and to validate each cleaning step prior to reuse for production of biopharmaceutical products.

Single use disposable bioreactor systems have been introduced to market as an alternative choice for biological product production. Such devices provide more flexibility on biological product manufactuwheel capacity and scheduling, avoid risking major upfront capital investment, and simplify the regulatory compliance requirements by eliminating the cleaning steps between batches. However, the mixing technology of the current disposable bioreactor system has limitations in terms of scalability to sizes beyond 200 liters and the expense of large scale units. Therefore, a disposable single use bioreactor system which is scaleable beyond 1000 liters, simple to operate, and cost effective will be needed as a substitute for conventional stainless steel bioreactors for biopharmaceutical research, development, and manufactuwheel. While several methods of mixing liquid in disposable bioreactors have been proposed in recent years, none of them provide efficient mixing in large scale (greater than 1000 liters) without expensive operating machinery.

SUMMARY OF THE INVENTION

The present invention is directed to a bioreactor with mixing apparatus including a rotational mixer in a containment vessel capable of efficiently and thoroughly mixing solutions without contamination. Large scale disposable units are also contemplated. The bioreactor includes a gas supply driving a rotational mixer having buoyancy driven mixing cavities.

In a first separate aspect of the present invention, the rotational mixer further includes two parallel wheels displaced from one another and blades disposed to induce flow axially through each wheel in opposite directions with rotation of the rotational mixer. Baffles fixed in the containment vessel to either side of the rotational mixer are inclined toward the rotational mixer in the direction of rotation.

In a second separate aspect of the present invention, the rotational mixer further includes two parallel wheels displaced from one another and blades disposed to induce flow axially through each wheel in opposite directions with rotation of the rotational mixer. Baffles fixed in the containment vessel to either side of the rotational mixer are inclined toward the rotational mixer in the direction of rotation. Outer paddies are disposed to mix and to induce rotational flow with rotation of the rotational mixer.

In a third separate aspect of the present invention, the rotational mixer further includes two parallel wheels displaced from one another and blades disposed to induce flow axially through each wheel in opposite directions with rotation of the rotational mixer. Battles fixed in the containment vessel to either side of the rotational mixer are inclined toward the rotational mixer in the direction of rotation. Outer paddies are disposed to mix and to induce rotational flow with rotation of the rotational mixer and inner paddles are disposed to mix and to induce rotational flow with rotation of the rotational mixer, the outer paddies being on opposite sides of the wheels from the inner paddles.

In a fourth separate aspect of the present invention, any of the foregoing aspects are contemplated to be employed in combination to greater advantage.

Accordingly, it is a principal object of the present invention to provide an improved pneumatic bioreactor. Other and further objects and advantages will appear hereinafter.

DETAILED DESCRIPTION OF THE PREFERRED EMBODIMENTS

Figure 1:
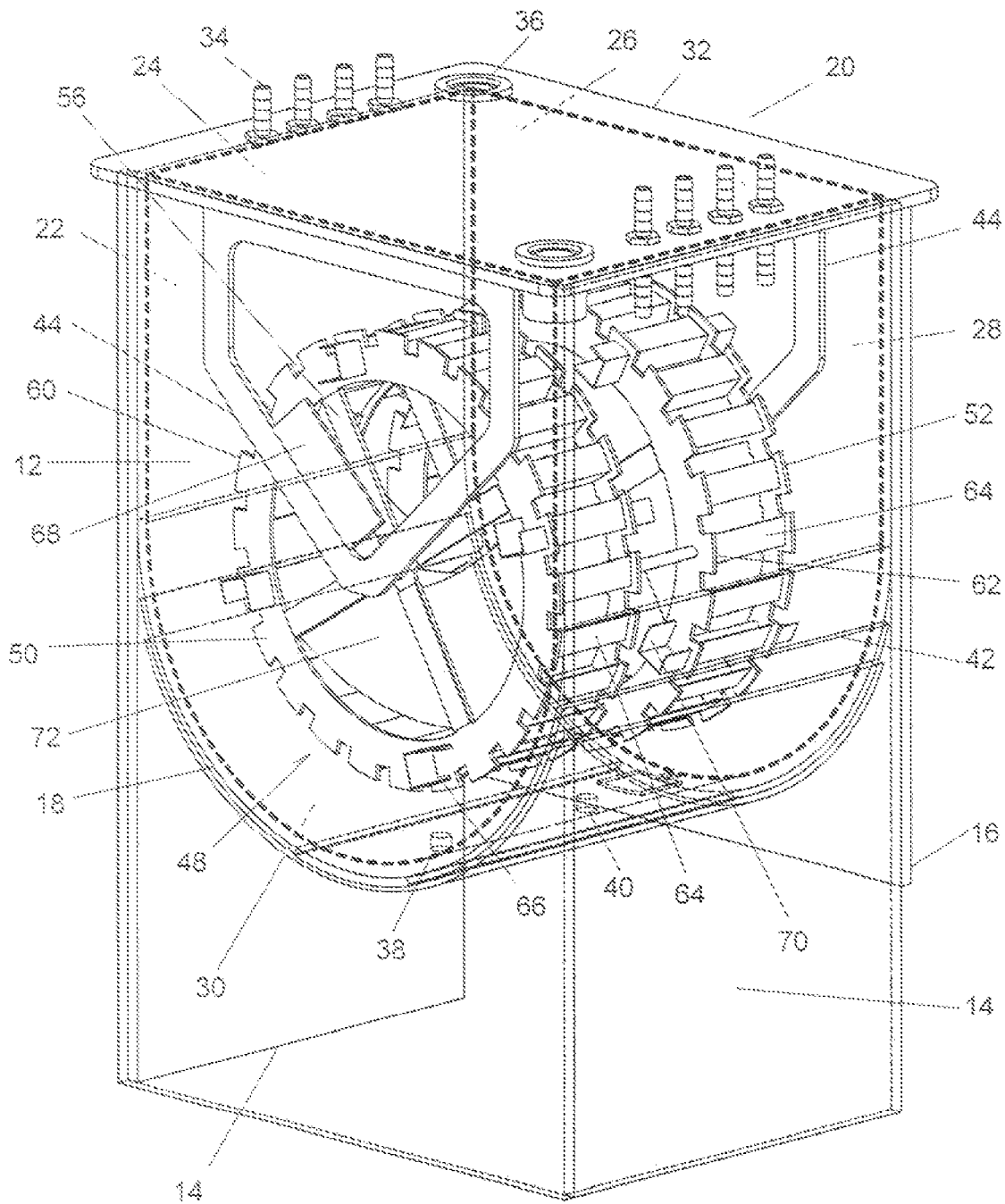
FIG. 1 is a perspective view of a pneumatic bioreactor shown through a transparent housing and containment vessel for clarify.

Turning in detail to the drawings, a bioreactor positioned in a housing, generally designated 10, is illustrated. The housing 10 is structural and preferably made of stainless steel to include a housing front 12, housing sides 14 and a housing back 16. The housing back 16 does not extend fully to the floor or other support in order that access may be had to the underside of the bioreactor. The housing 10 includes a housing bottom 18 which extends from the housing sides 14 in a semi-cylindrical curve above the base of the housing 10. One of the front 12 or back 16 may act as a door to facilitate access to the interior of the housing 10.

The bioreactor includes a containment vessel, generally designated 20, defined by four vessel sides 22, 24, 26, 28, a semi-cylindrical vessel bottom 30 and a vessel top 32. Two of the vessel sides 24, 28 which are opposed each include a semicircular end. The other two vessel sides 22, 28 join with the semi-cylindrical vessel bottom 30 to form a continuous cavity between the two vessel sides 24, 28. All four vessel sides 22, 24, 28, 28 extend to and are sealed with the vessel top 32 to form a sealed enclosure. The vessel top 32 extends outwardly of the four vessel sides 22, 24, 26, 28 so as to rest on the upper edges of the structural housing front 12, sides 14 and back 16. Thus, the containment vessel 20 hangs from the top 32 in the housing 10. The vessel 20, with the exception of the vessel top 32, is of thin wall film which is not structural in nature. Therefore, the housing front 12, sides 14, back 16 and bottom 18 structurally support the containment vessel 20 depending from the vessel top 32 when filled with liquid. All joints of the containment vessel 20 are welded or otherwise sealed to provide the appropriate sealed enclosure which can be sterilized and dosed ready for use.

The vessel top 32 includes access ports 34 for receipt or extraction of liquids, gases and powders and grains of solid materials. The access ports 36 in the vessel top 32 provide for receipt of sensors to observe the process. Two orifices 38, 40 are shown at the vessel bottom 30 slightly offset from the centerline to receive propellant gas for driving line rotational mixer as will be discussed below. The semi-cylindrical vessel bottom 30 defining a semi-cylindrical concavity within the containment vessel 20 also includes a temperature control sheet 42 which may include a heater with heating elements, a cooler with cooling coils, or both, as may be employed to raise or lower the temperature of the contents of the containment vessel 20 during use. Sealed within the enclosure defining the containment vessel 20, struts 44 extend downwardly from the vessel top 32 to define a horizontal mounting axis at or close to the axis of curvature defined by the semi-cylindrical bottom 30.

A mixing apparatus includes a rotatably mounted rotational mixer, generally designated 48. The rotational mixer 48 is a general assembly of a number of functional components. The structure of the rotational mixer 48 includes two parallel wheels 50, 52 which are displaced from one another. These wheels are tied to an axle 54 by spokes 56. Additional stabilizing bars parallel to the axle 54 may be used to rigidity the rotational mixer 48.

Each wheel 50, 52 is defined by two parallel plates 60, 62. These plates 80, 62 include buoyancy-driven mixing cavities 84 there between. These cavities 64 operate to entrap gas supplied from below the wheels 50, 52 through the gas supply at orifices 38, 40. The orifices 38, 40 are offset from being directly aligned with the horizontal axis of rotation to insure that the buoyancy-driven cavities 64 are adequately filled with gas to power the rotational mixer 48 in rotation. The buoyancy-driven cavity 64 in each one of the wheels 50, 52 are similarly oriented to receive gas from the orifices 38, 40 at the same time.

Outer paddies 66 are equiangularly placed to extend axially outwardly from the outer parallel plates 60 where they are attached. These outer paddles 66 can mix the liquid between the rotational mixer 48 and either side 24, 28. The outer paddies 66 are formed in this embodiment with a concavity toward the direction of rotation of the rotational mixer 48 to induce flow entrained with constituents of the mix in the vessel 20 rotationally to lift constituents of the mix from the bottom of the containment vessel 20 with the rotation of the rotational mixer 48. The number of outer paddles 66 may be increased from the four shown, particularly when the constituents of the mix in the vessel 20 are not easily maintained in suspension. The outer paddles 66 are adjacent the periphery of the outer parallel plates 60 and may extend close to the vessel bottom 30 to entrain constituents of the mix in the vessel 20 which can otherwise accumulate on the bottom.

Any extensions beyond the wheels 50, 52 preferably do not inhibit rotation of the rotational mixer 48 through actual or close interaction with the vessel wall.

Stationary baffles 68 are fixed in the containment vessel 20, conveniently to the struts 44, on either side of the rotational mixer. These baffles 68 are inclined toward the rotational mixer in the direction of rotation. As rotational flow is induced buy the rotation of the wheels 50, 52, the stationary baffles 68 redirect that flow to the inner portions of the wheels 50, 52. The rotational flow is further enhanced by the outer paddles 66. The baffles 68 are arranged inwardly of the outer paddies 66 for clearance. There may be additional baffles 68 which could either be included on the struts 44 or through the provision of additional structural support.

Inner paddles 70 extend axially inwardly from the inner parallel plates 62. These inner paddles 70 are convex facing toward the rotational direction to induce rotational flow entrained with constituents of the mix in the vessel 20 rotationally to lift constituents of the mix from the bottom of the containment vessel 20 with the rotation of the rotational mixer 48. The number of inner paddles 70 may be increased from the four shown, particularly when the constituents of the mix in the vessel 20 are not easily maintained in suspension. The inner paddles 70 are adjacent the periphery of the inner parallel plates 62 and may extend close to the vessel bottom 30 to entrain constituents of the mix in the vessel 20 which can otherwise accumulate on the bottom. Any extensions beyond the wheels 50, 52 preferably do not inhibit rotation of the rotational mixer 48 through actual or close interaction with the vessel wall.

Located inwardly of each wheel 50, 52 is an impeller having blades 72. The two impellers provide principal axial thrust to the flow through the wheels 50, 52. The thrust resulting from these blades 72 both flow inwardly toward one another in this embodiment. This is advantageous in creating toroidal flow about the wheels and balance forces which would otherwise be imposed on the mountings. The placement of the blades 72 may be at other axial locations such as at either of the plates 60, 62.

The mixing apparatus defined principally by the rotating rotational mixer 48 is positioned in the containment vessel 20 such that it extends into the semi-cylindrical concavity defined by the vessel bottom 30 and is sized, with the outer paddles 66 and inner paddies 70, to fill the concavity but for sufficient space between the mixing apparatus and the vessel sides 24, 28 and bottom 30 to avoid inhibiting free rotation of the rotational mixer 48. In one embodiment, the full extent of the mixing apparatus 26 is on the order of 10% smaller than the width of the cavity in the containment vessel 20 and about the same ratio for the diameter of the rotational mixer 48 to the semi-cylindrical vessel bottom 30. This spacing is not critical so long as the mixing apparatus is close enough and with commensurate speed to effect mixing throughout the concavity. Obviously, empirical testing is again of value. The liquid preferably does not extend above the mixing apparatus and the volume above the rotational mixer 48 will naturally be mixed as well.

Figure 2:
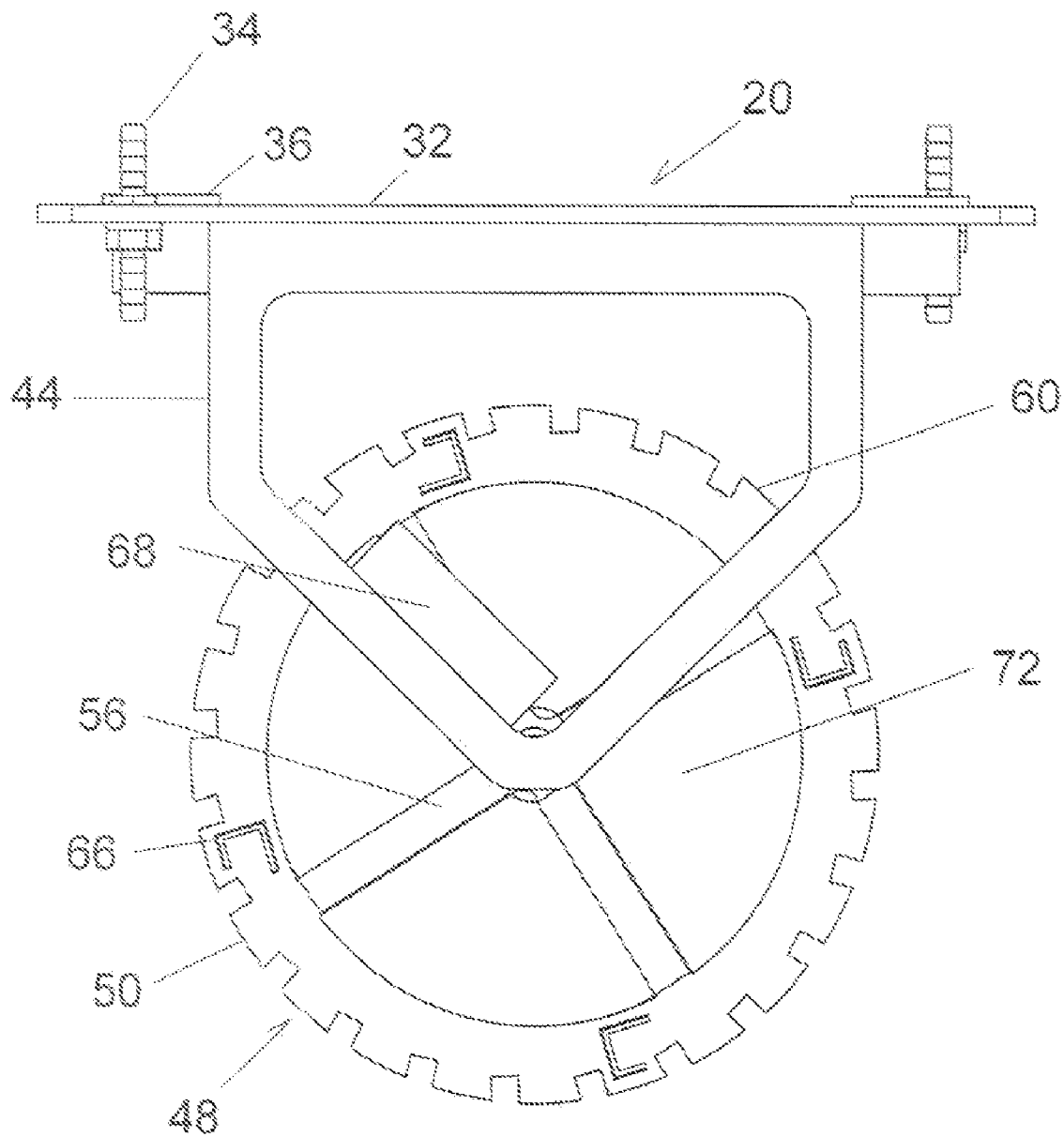
FIG. 2 is a front view of the pneumatic bioreactor of FIG. 1.
Figure 3:
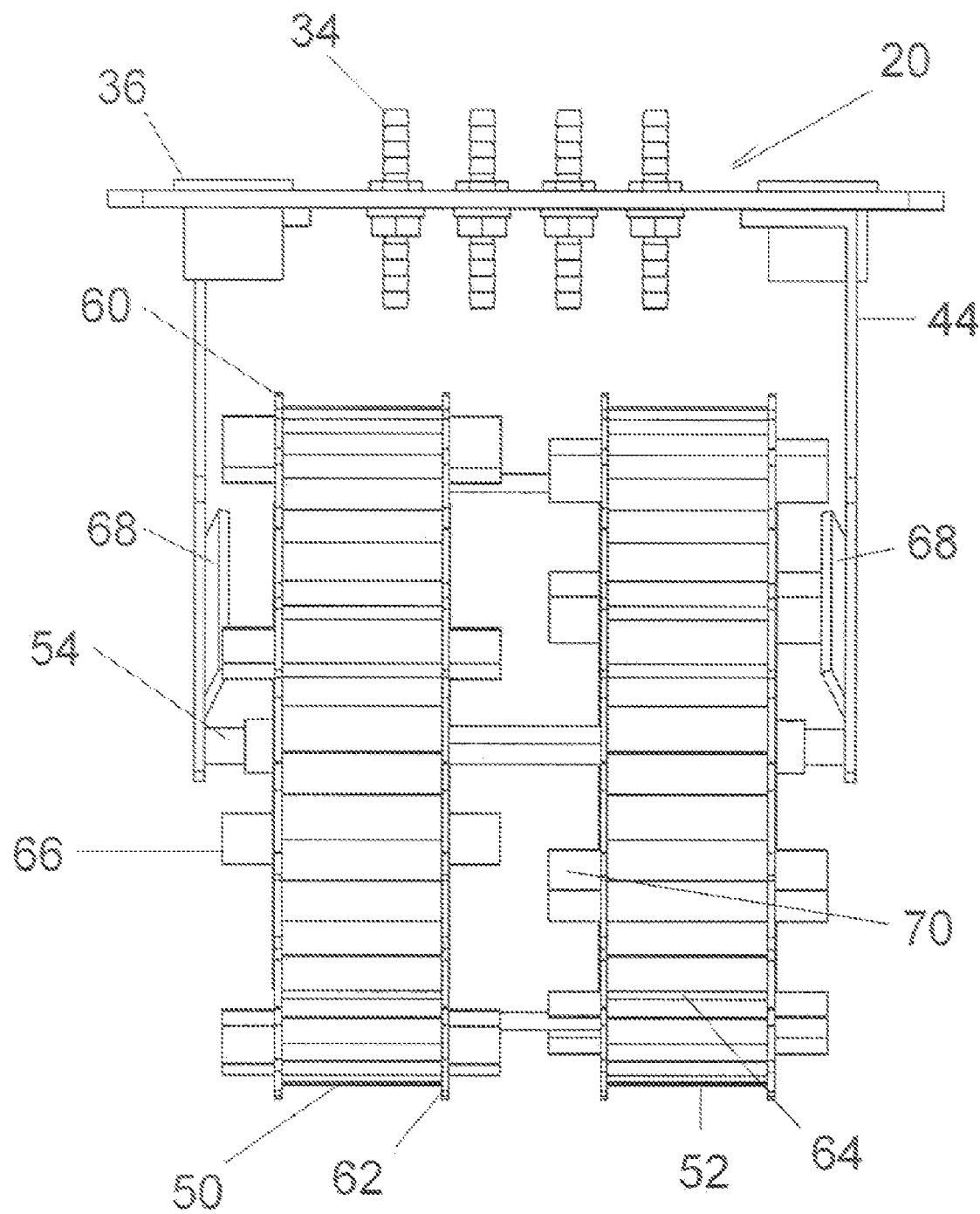
FIG. 3 is side view of the pneumatic bioreactor of FIG. 1.
Figure 4:
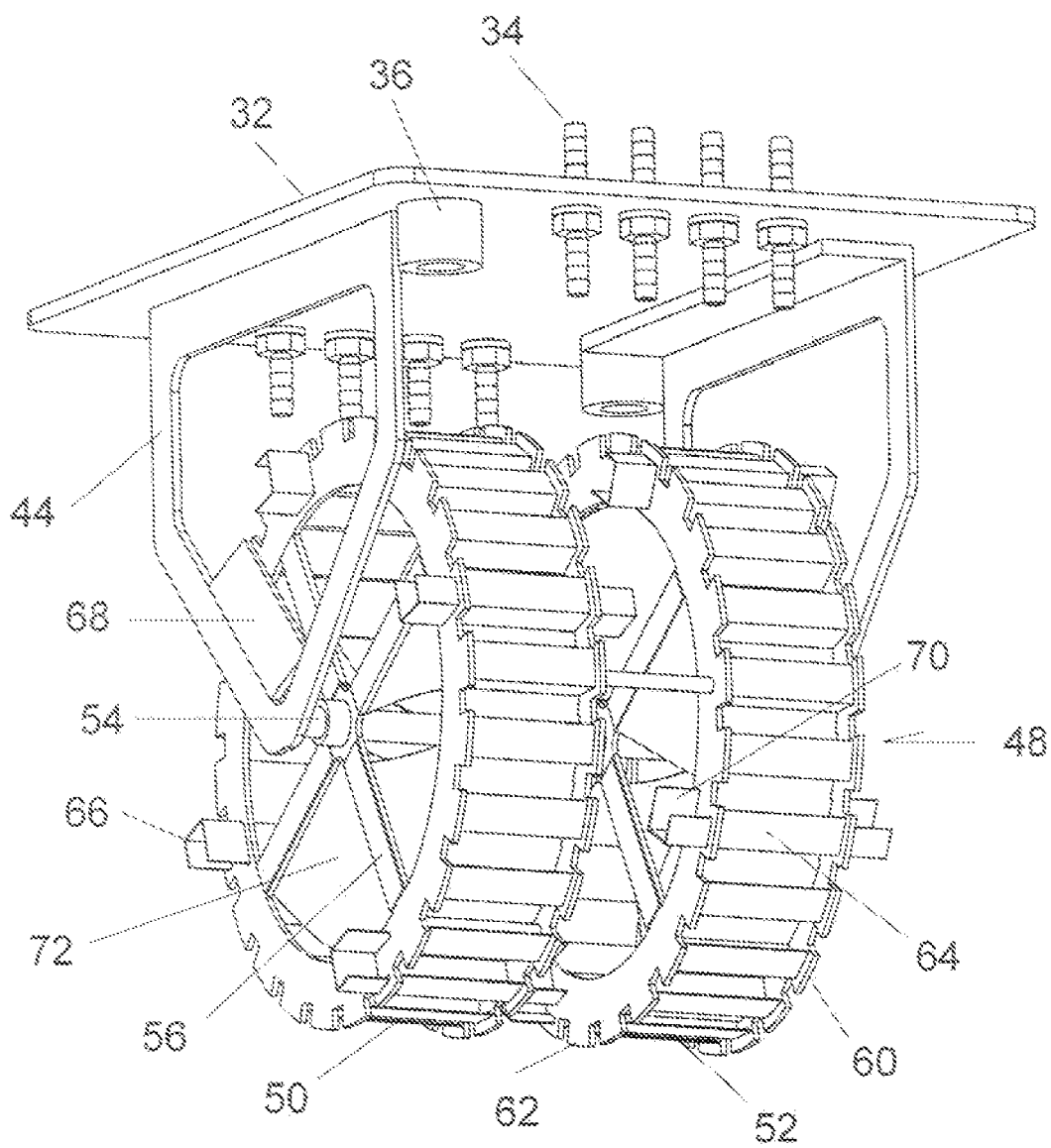
FIG. 4 is a perspective view of the top and mixing apparatus of the pneumatic bioreactor of FIG. 1.

In operation, the liquid, nutrients and active elements are introduced into the containment vessel 20 through the ports 34, 36. The level of material in the vessel 20 is below the top of the rotational mixer 48 to avoid the release of driving gas under the liquid surface which may cause foam. Gas is injected through the orifices 38, 40 to become entrapped in the buoyancy-driven cavity 64 in the rotational mixer 48. This action drives the rotational mixer 48 in a direction which is seen as clockwise in FIG. 2.

The blades 72 act to circulate the liquid within the containment vessel 20 with toroidal flow in opposite directions through the wheels 50, 52, radially outwardly from between the wheels 50, 52 and then radially inwardly on the outsides of the rotational mixer 48 to again be drawn into the interior of the rotational mixer 48. Mixing with turbulence is desired and the outer paddles 66, the stationary baffles 68 and the inner paddles 70 contribute to the mixing and to the toroidal flow about each of the wheels 50, 52. The target speed of rotation is on the order of up to the low tens of rpm to achieve the similar mixing results as prior devices at 50 to 300 rpm. The difference may reduce shear damage in more sensitive materials. Oxygen may be introduced in a conventional manner as well as part of the driving gas to be mixed fully throughout the vessel 20 under the influence of the mixing apparatus.

Thus, an improved pneumatic bioreactor is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A pneumatic bioreactor comprising
   a containment vessel;
   a gas supply having at least one orifice in the containment vessel;
   mixing apparatus including a rotational mixer rotatably mounted in the containment vessel about a horizontal axis, the rotational mixer comprising:
   buoyancy-driven mixing cavities above the at least one orifice,
   two parallel wheels displaced from one another,
   blades disposed to induce flow axially through the wheels in opposite directions with rotation of the rotational mixer,
   baffles fixed in the containment vessel to either side of the rotational mixer and inclined toward the rotational mixer in the direction of rotation,
   outer paddles disposed to mix and to induce rotational flow with rotation of the rotational mixer, and
   inner paddles to mix and to induce rotational flow radially with rotation of the rotational mixer, the outer paddles being on opposite sides of the wheels from the inner paddles.

2. The pneumatic bioreactor of claim 1, each of the wheels having two parallel plates, the buoyancy-driven mixing cavities extending between the parallel plates in each wheel there being two of the at least one orifice under the buoyancy-driven mixing cavities of the wheels, respectively.

3. The pneumatic bioreactor of claim 1, wherein each of the outer paddles comprises three wall segments extending laterally from an outer side of one of the wheels and interconnected so as to define a partial enclosure that is open in one direction.

4. The pneumatic bioreactor of claim 1, wherein each of the inner paddles comprises three wall segments extending laterally from an inner side of one of the wheels and interconnected so as to define a partial enclosure that is open in one direction.

* * * * *